US010792004B2

(12) United States Patent
Patel

(10) Patent No.: US 10,792,004 B2
(45) Date of Patent: Oct. 6, 2020

(54) DIFFERENTIAL DIAGNOSIS OF PERIAPICAL DISEASES BASED ON RESULTS OF IMAGE ANALYSIS

(71) Applicant: Rutgers, The State University of New Jersey, New Brunswick, NJ (US)

(72) Inventor: Jay Sureshbhal Patel, Indianapolis, IN (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 227 days.

(21) Appl. No.: 15/776,014

(22) PCT Filed: Nov. 11, 2016

(86) PCT No.: PCT/US2016/061615
§ 371 (c)(1),
(2) Date: May 14, 2018

(87) PCT Pub. No.: WO2017/083709
PCT Pub. Date: May 18, 2017

(65) Prior Publication Data
US 2018/0325484 A1    Nov. 15, 2018

Related U.S. Application Data

(60) Provisional application No. 62/254,979, filed on Nov. 13, 2015.

(51) Int. Cl.
*A61B 6/14* (2006.01)
*G06T 7/00* (2017.01)
(Continued)

(52) U.S. Cl.
CPC .............. *A61B 6/5217* (2013.01); *A61B 6/14* (2013.01); *A61B 6/505* (2013.01); *A61B 6/563* (2013.01);
(Continued)

(58) Field of Classification Search
None
See application file for complete search history.

(56) References Cited

U.S. PATENT DOCUMENTS

2002/0186875 A1* 12/2002 Burmer .............. G06K 9/00127
382/133
2003/0112921 A1   6/2003 Lang et al.
(Continued)

FOREIGN PATENT DOCUMENTS

WO        9111959 A1    8/1991
WO    20140174317 A2   10/2014

OTHER PUBLICATIONS

Razavian et al.: "An In Vitro Comparative Study of a Digital and Conventional Imaging System for Detection of Endodontic Procedural Errors", 2014, Indian J. Sci. Res, vol. 4, No. 3, pp. 430-436.
(Continued)

*Primary Examiner* — Idowu O Osifade
(74) *Attorney, Agent, or Firm* — Fox Rothschild LLP

(57) ABSTRACT

Systems (100) and methods (200, 1600) for generating a medical and/or dental diagnosis. The methods comprise: obtaining a true color image of a select part of a subject's body; converting the true color image to a grayscale intensity image; generating a histogram equalized image by adjusting the grayscale intensity image's contrast; processing the histogram equalized image to generate first information useful for generating the medical and/or dental diagnosis, the first information comprising at least one of (a) a ratio of a disease region's pixel mean intensity value and
(Continued)

a normal region's mean pixel intensity value and (b) an indicator indicating whether a periodontal ligament space has widened or broken; and generating the medical and/or dental diagnosis based at least on the first information.

20 Claims, 9 Drawing Sheets

(51) Int. Cl.
*G16H 30/40* (2018.01)
*G16H 10/60* (2018.01)
*A61B 6/00* (2006.01)
*G06T 7/62* (2017.01)
*G06T 5/00* (2006.01)
*G06T 5/40* (2006.01)

(52) U.S. Cl.
CPC ............... *G06T 5/009* (2013.01); *G06T 5/40* (2013.01); *G06T 7/0012* (2013.01); *G06T 7/62* (2017.01); *G16H 10/60* (2018.01); *G16H 30/40* (2018.01); *G06T 2207/10024* (2013.01); *G06T 2207/10116* (2013.01); *G06T 2207/30008* (2013.01); *G06T 2207/30036* (2013.01)

(56) References Cited

U.S. PATENT DOCUMENTS

| | | |
|---|---|---|
| 2003/0191368 A1 | 10/2003 | Wang et al. |
| 2004/0209237 A1 | 10/2004 | Flewelling et al. |
| 2006/0072799 A1 | 4/2006 | McLain |
| 2006/0195342 A1 | 8/2006 | Khan et al. |
| 2010/0023351 A1 | 1/2010 | Lifshits et al. |
| 2012/0148986 A1 | 6/2012 | Yan et al. |
| 2013/0286174 A1 | 10/2013 | Urakabe |
| 2014/0068255 A1 | 3/2014 | Park et al. |
| 2014/0316284 A1 | 10/2014 | Rege et al. |
| 2017/0281280 A1* | 10/2017 | Haider ............... A61B 17/1703 |

OTHER PUBLICATIONS

Grondahl, H.G.: "Digital Radiology in Dental Diagnosis: A Critical View"; Dentomaxillofac. Radiol., 1992, vol. 21, pp. 198-202.

Sogur, et al., "Pixel Intensity and Fractal Dimension of Periapical Lesions Visually Indiscernible in Radiographs", Joe, Jan. 2013, vol. 39, No. 1, pp. 16-19.

Sharmila, et al., "Detection of Dental Plaque Using Image Processing"; International Law of Journal of Advanced Information Science and Technology, Oct. 2013, vol. 18, No. 18, pp. 61-65.

Oprea, et al.; "Image Processing Techniques Used for Dental X-Ray Image Analysys"; Electronics Technology, ISSE 2008, pp. 125-129.

Selinummi, et al.: "Software for Quantification of Labeled Bacteria from Digital Microscope Images by Automated Image Analysis"; BioTechniques, 2005, vol. 39, No. 6, pp. 859-862.

* cited by examiner

True Color Image

Histogram Equalized Image

Grayscale Intensity Image

Contour Plot of Histogram Equalized Image

DIFFERENTIAL DIAGNOSIS OF PERIAPICAL DISEASES BASED ON RESULTS OF IMAGE ANALYSIS

CROSS-REFERENCE TO RELATED APPLICATIONS

This patent application claims the benefit of International Application No. PCT/US16/61615 filed on Nov. 11, 2016, which claims the benefit of U.S. Provisional Ser. No. 62/254,979 filed Nov. 13, 2015, all of which are incorporated by reference herein in their entirety.

FIELD

This document relates generally to image processing. More particularly, this document relates to systems and methods for the differential diagnosis of periapical diseases based on results of image analysis.

BACKGROUND

There are various image processing techniques known in the art. In such image processing techniques, an input digital image may be processed to generate a set of characteristics or parameters related thereto. A digital image is a collection of pixels laid out in a specific order with a width x and a height y. A pixel is a smallest picture element of the image. Each pixel has a numerical color value, a numerical size/spatial value, and/or intensities associated therewith. The numerical values comprise binary numbers of at least one (1) bit. For example, a monochrome pixel can have two (2) color values, 0 (e.g., representing the color black) or 1 (e.g., representing the color white). Color or gray scale pixels require more bits (e.g., 24 bits) for representing each color. The intensity of each pixel is variable. In color image systems, a color is typically represented by three (3) component intensities such as red, green and blue. Other component intensities may include cyan, magenta, yellow and/or black.

SUMMARY

The present disclosure generally concerns systems and methods for generating a medical and/or dental diagnosis. The methods comprise: obtaining, by a computing device, a true color image of a select part of a subject's body; converting, by the computing device, the true color image to a grayscale intensity image; generating, by the computing device, a histogram equalized image by adjusting the grayscale intensity image's contrast; and processing, by the computing device, the histogram equalized image to generate first information useful for generating the medical and/or dental diagnosis. The first information comprises at least one of (a) a ratio of a disease region's pixel mean intensity value and a normal region's mean pixel intensity value and (b) an indicator indicating whether a periodontal ligament space has widened or broken (indicating whether the lesion is abscess, granuloma or cyst). The first information is then used to generate the medical and/or dental diagnosis by a computing device. Information specifying the medical and/or dental diagnosis may be encrypted prior to being stored in a data store or communicated over a network.

In some scenarios, the processing involves: generating a contour plot of the histogram equalized image so that normal and abnormal bone density regions of the histogram equalized image are identifiable; generating a color map of the histogram equalized image so that root canals (including accessory canals that are difficult to identify by an eyeballing technique) are identifiable; and/or generating a red image, a green image, or a blue image so that variations in canal dimensions are identifiable.

In those or other scenarios, the methods also comprise transforming the medical and/or dental diagnosis into a more accurate medical and/or dental diagnosis using clinical symptoms specified in the subject's medical records. This transformation can involve determining whether the clinical symptoms in the subject's medical records match clinical symptoms of a medical and/or dental condition identified by the medical and/or dental diagnosis. If so, the accuracy of the medical and/or dental condition is verified or validated. In not, the medical and/or dental diagnosis is determined to be inaccurate. Accordingly, the first information and medical record information is re-analyzed to derive the more accurate medical and/or dental diagnosis.

In those or yet other scenarios, the medical and/or dental diagnosis is generated based additionally on clinical symptoms specified in the subject's medical records. More specifically, the medical and/or dental diagnosis is generated by: obtaining a first differential diagnosis based on the clinical symptoms; and validating an accuracy of the first differential diagnosis using the first information. Alternatively, the medical and/or dental diagnosis is generated by: obtaining a first differential diagnosis based on the clinical symptoms; obtaining a second differential diagnosis based on the first information; and determining the medical and/or dental diagnosis based on the first differential diagnosis and second differential diagnosis.

DESCRIPTION OF THE DRAWINGS

Embodiments will be described with reference to the following drawing figures, in which like numerals represent like items throughout the figures.

DETAILED DESCRIPTION

Figure 1:
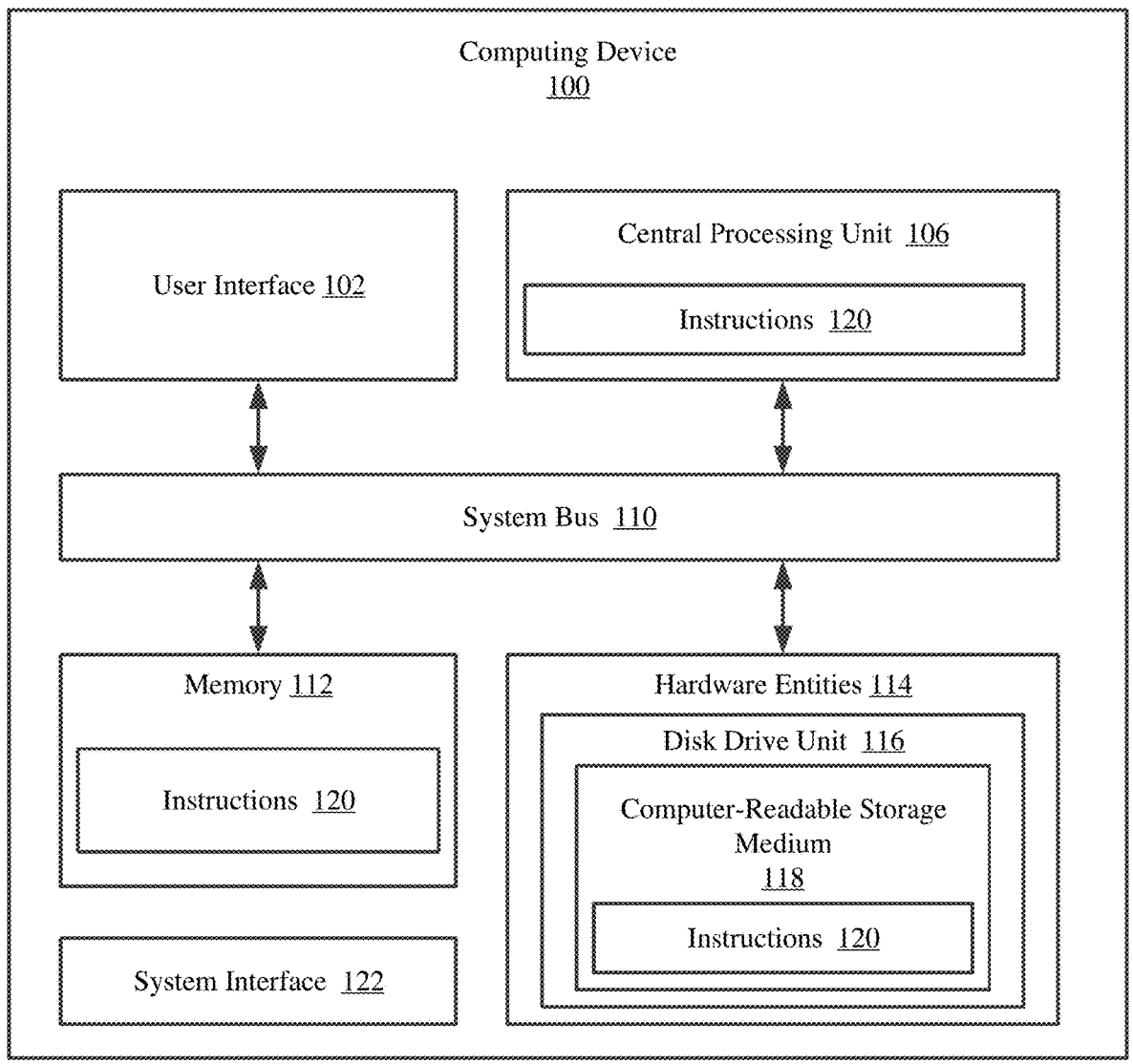
FIG. 1 is a schematic illustration of an exemplary computing device.

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present solution may be embodied in other specific forms without departing from its spirit or essential characteristics. The described embodiments are to be considered in all respects only as illustrative and not restrictive. The scope of the present solution is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present solution should be or are in any single embodiment of the invention. Rather, language referring to the features and advantages is understood to mean that a specific feature, advantage, or characteristic described in connection with an embodiment is included in at least one embodiment of the present solution. Thus, discussions of the features and advantages, and similar language, throughout the specification may, but do not necessarily, refer to the same embodiment.

Furthermore, the described features, advantages and characteristics of the present solution may be combined in any suitable manner in one or more embodiments. One skilled in the relevant art will recognize, in light of the description herein, that the present solution can be practiced without one or more of the specific features or advantages of a particular embodiment. In other instances, additional features and advantages may be recognized in certain embodiments that may not be present in all embodiments of the present solution.

Reference throughout this specification to "one embodiment", "an embodiment", or similar language means that a particular feature, structure, or characteristic described in connection with the indicated embodiment is included in at least one embodiment of the present solution. Thus, the phrases "in one embodiment", "in an embodiment", and similar language throughout this specification may, but do not necessarily, all refer to the same embodiment.

As used in this document, the singular form "a", "an", and "the" include plural references unless the context clearly dictates otherwise. Unless defined otherwise, all technical and scientific terms used herein have the same meanings as commonly understood by one of ordinary skill in the art. As used in this document, the term "comprising" means "including, but not limited to".

The present disclosure concerns systems and methods for the computerized differential diagnosis of periapical pathologies using an image processing toolbox to improve efficiency of diagnosis. The main concept is to identify pixel intensities, distance between the periodontal ligament space and measure of an alveolar bone pattern, and secondarily to give effects to an image to differential different structures (e.g., accessory canals, automatic identification of bone loss and identification of cracked tooth syndrome). As such, the present technology is in the emerging field of Dental informatics comprising an application of computer science, information science and dental science to improve dental diagnostics. The present technology allows standard x-rays to be analyzed for providing information on sometimes non-observable disease, infections (e.g., apical periodontitis, periapical abscesses), tooth and tissue conditions (including density and radio-lucence, recognized indicators), pathologies, locations, and related beyond what reading of an x-ray may provide (including cases where x-rays do not indicate any disease issues at all). Simulated tests have demonstrated high sensitivity, specificity and accuracy helpful for early or difficult detection and differential diagnosis which can prevent major surgical and invasive procedures.

In practice, different effects and readings can be given to conventional x-rays. The present technology can also provide slicing simulation for multi-dimensional determinations of volume and depth of issue. Machine learning gives an option to clinicians to use the present technology not only for endodontic purpose, but also for Periodontic purposes, Pedodontic purposes, Prosthodontic purposes and Oral Diagnosis purposes. Using this machine learning, based on the input of different cases of x-rays with or without conditions, the computer can learn and get trained on diagnosis vast area of different cases. This tool also includes a machine learning algorithm to train the system to diagnose different cases.

In some scenarios, MatLab® Software is used to implement the present methods. The present technique is not limited in this regard. The present technique can additionally or alternatively be implemented using any known or to be known computer language (e.g., C++, Java, HTML, etc.). The MatLab® Software is used to write code implementing algorithms for the image processing toolbox. Exemplary code is provided below.

```
% --- Executes on a button press to convert an image to grayscale.
function pushbutton1_Callback(hObject, eventdata, handles)
global filename;
filename = uigetfile;
I = imread(filename);
gray=rgb2gray(I);
imshow(gray);
% --- Executes on a button press to perform histogram equalization.
function pushbutton2_Callback(hObject, eventdata, handles)
global filename;
I =imread(filename);
gr=rgb2gray(I);
hs=histeq(gr);
imshow(hs);
% --- Executes on a press of a bone density function button to generate a contour plot useful for identifying regions of bone loss.
function pushbutton3_Callback(hObject, eventdata, handles)
```

-continued

```
global filename;
I =imread(filename);
gr=rgb2gray(I);
imcontour(gr)
% --- Executes on a press of a canal identification function to generate a color map useful for
identifying root canals, especially accessory root canals.
function pushbutton5_Callback(hObject, eventdata, handles)
global filename;
I =imread(filename);
colormap default
% --- Executes on a press of a color extraction function to generate a green image useful for
more easily identifying variations in canal dimensions that may indicate the presence of an
abscess.
function pushbutton8_Callback(hObject, eventdata, handles)
    global filename;
I =imread(filename);
I(:,:,1) = 0;
    I(:,:,3)= 0;
    imshow(I);
% --- Executes on a press of a pixel intensity function to compute a pixel mean intensity value
useful for confirming or verifying a diagnosis by medical practitioners. A user will be prompted
to select two regions within a displayed image. A first region comprises the region which a
clinician believes may have a disease. A second region comprises a region which the clinician
believes is a normal, non-diseased region. The tool automatically takes the ratio of the first and
second regions' pixel intensities, and categorizes the ration in-between 0 and 1. Based on the
ratio, the tool will give one diagnosis.
global filename;
I =imread(filename);
gcv=rgb2gray(I);
hs=histeq(gcv);
pix=impixel(hs);
avg=mean(pix);
ratio=first region/second region;
```

This process is also automatically programmed using machine learning algorithms. Where, a clinician can also train the system based on the lesions. After achieving desirable accuracy, sensitivity and specificity, the manual selection function will be eliminated and the computer will automatically diagnose the disease. Exemplary code for machine learning is provided below.

```
Training algorithm:
clc
close all
clear all
load svmStruct
%% read image
[filename filepath]=uigetfile('*.bmp;*.jpg;*.png','Load image');
if filename==0
                return;
end
im=imread([filepath, filename]);
% im = imread('lung1.jpg');
if size(im,3)==3
                im = rgb2gray(im);
end
figure(1),imshow(im);
% % im2=histeq(im);
% im2=adapthisteq(im);
% figure,imshow(im2);
K = imadjust(im,stretchlim(im),[ ]);
figure(2),imshow(K)
R1=K;
b=round(size(K,2)/15);
%% 3.4 Feature extraction
figure(3),imshow(R1); title('Blocks');
hold on
[r,c]=size(R1);
m1=floor(r/b);
```

-continued

```
n1=floor(c/b);
map=zeros(m1,n1);
m=0;
for i=1:b:r-b
            n=0;
            m=m+1;
            for j=1:b:c-b
                    n=n+1;
                    blk=double(R1(i:i+b-1,j:j+b-1));
                    rectangle('position',[j,i,b,b],'edgecolor','r');
                    map(m,n)=1;
            end
end
hold off
% h1=msgbox('Click on boxes to be ignored');
% figure(3)
% [x y]=ginput; %Press enter to terminate
% % hold on
% % scatter(x,y);
% % hold off
% x = ceil(x/b);
% y = ceil(y/b);
%
% for i=1:length(x)
%           n=x(i);
%           m=y(i);
%           map(m,n)=2;
% end
% map
figure(3)
hold on
[r,c]=size(R1);
m=0;
disp('Processing...');
for i=1:b:r-b
            n=0;
            m=m+1;
            for j=1:b:c-b
               n=n+1;
               if map(m,n)==2
                    continue
               else
                 blk=double(R1(i:i+b-1,j:j+b-1));
                 rectangle('position',[j,i,b,b],'edgecolor','m');
                 min_b=min(blk(:));
                 mean_b=mean(blk(:));
                 var_b=var(blk(:));
                 moment3=mean((blk(:)-mean_b).^3);
                 moment4=mean((blk(:)-mean_b).^4);
                 moment5=mean((blk(:)-mean_b).^5);
                 LP5=LBP(blk,2);
                 H=hist((LP5(:)),16);
                 feat=[var_b,moment3,moment4,moment5,H];
                 clas = svmclassify(svmStruct,feat);
                 if clas==0
%                          disp('Diseased!');
                            rectangle('position',[j+5,i+5,b-10,b-10],'edgecolor','y');
%                          scatter(i+round(b/2),j+round(b/2),[ ],'r');
                 end
              end
           end
end
hold off
disp('Processing finished.');
databse builder:
clc
close all
clear all
tt=input('Enter 1 to add to existing database, 0 to start new ');
if tt==0
          XV=[ ];YV=[ ];
else
          load('Xydata.mat');
end
%% read image
[filename filepath]=uigetfile('*.bmp;*.jpg;*.png','Load image');
if filename==0
            return;
end
```

-continued

```
im=imread([filepath,filename]);
% im = imread('lung1.jpg');
if size(im,3)==3
        im = rgb2gray(im);
end
figure(1),imshow(im);
% % im2=histeq(im);
% im2=adapthisteq(im);
% figure,imshow(im2);
K = imadjust(im,stretchlim(im),[ ]);
figure(2),imshow(K)
R1=K;
b=round(size(K,2)/15);
%% 3.4 Feature extraction
figure(3),imshow(R1); title('Blocks');
hold on
[r,c]=size(R1);
m1=floor(r/b);
n1=floor(c/b);
map=zeros(m1,n1);
m=0;
for i=1:b:r-b
        n=0;
        m=m+1;
        for j=1:b:c-b
            n=n+1;
            blk=double(R1(i:i+b-1,j: j+b-1));
            rectangle('position',[j,i,b,b],'edgecolor','r');
            map(m,n)=2;
        end
end
hold off
figure(3),title('Click on diseased blocks');
h=msgbox('Click on diseased boxes using mouse and click enter button to end');
[x y]=ginput; %Press enter to terminate
hold on
scatter(x,y);
hold off
x = ceil(x/b);
y = ceil(y/b);
for i=1:length(x)
        n=x(i);
        m=y(i);
        map(m,n)=0;
end
figure(3),title('Click on healthy boxes');
h1=msgbox('Click on healthy boxes');
[x y]=ginput; %Press enter to terminate
hold on
scatter(x,y);
hold off
x = ceil(x/b);
y = ceil(y/b);
for i=1:length(x)
        n=x(i);
        m=y(i);
        map(m,n)=1;
end
map
figure(3),title('To be added to database')
hold on
[r,c]=size(R1);
m=0;
for i=1:b:r-b
        n=0;
        m=m+1;
        for j=1:b:c-b
            n=n+1;
            if map(m,n)==2
              continue
            else
              blk=double(R1(i:i+b-j:j+b-1));
              if map(m,n)==0
                rectangle('position',[j,i,b,b],'edgecolor','y');
              else
                rectangle('position',[j,i,b,b],'edgecolor','g');
              end
              min_b=min(blk(:));
              mean_b=mean(blk(:));
```

```
                var_b=var(blk(:));
                moment3=mean((blk(:)-mean_b).^3);
                moment4=mean((blk(:)-mean_b).^4);
                moment5=mean((blk(:)-mean_b).^5);
                LP5=LBP(blk,2);
                H=hist((LP5(:)),16);
                feat=[var_b,moment3,moment4,moment5,H];
                XV=[XV;feat];
                YV=[YV;map(m,n)];
            end
        end
end
hold off
save Xydata.mat XV YV ; % eigvector;
size(XV)
size(YV)
Training:
load Xydata.mat
in0=find(YV==0)
in1=find(YV==1);
Y0=YV(in0);
Y1=YV(in1);
X0=XV(in0,:);
X1=XV(in1,:)
XV=[X0;X1]
YV=[Y0;Y1]
svmStruct = svmtrain(XV,YV,'showplot',true);
classes = svmclassify(svmStruct,XV);
err=sum(abs(YV-classes))
acc=(length(YV)-err)/length(YV)
save svmStruct svmStruct
```

As shown by the above code, the radiographic images are analyzed using different functions and effects present in the image processing toolbox. These functions facilitate an identification of normal/disease regions, bone loss regions, and accessory canal regions. The regions of bone loss are identified by measuring the bone densities of a periapical region and detecting changes in the measured bone densities.

The following EXAMPLE is provided in order to further illustrate the present solution. The scope of the present solution, however, is not to be considered limited in any way thereby.

EXAMPLE

In some scenarios, the methods involve: collecting radiographic images; analyzing the radiographic images using different functions of the image processing toolbox; diagnosing first and second sets of results using functions and intensity levels of periapical region; and comparing the first and second sets of results.

The results specify the following four (4) different classes that are useful for making a diagnosis:
(1) Class 1—No Abnormality/Pathogenesis: Intensity Ratio 0.8-1.0 and no widening of Periodontal Ligament ("PDL") space;
(2) Class 2—Apical Periodontitis: Intensity Ratio 0.8-1.0 and widening of the PDL space up to 25;
(3) Class 3—Periapical Abscess/Granuloma: Intensity Ratio in-between 0.25-0.70 and broken PDL space; and
(4) Class 4—Periapical Cyst, Periapical Abscess: Intensity Ratio less than 0.25 and broken PDL space.

Out of thirty (30) radiographic images, eight (8) images were found with intensity ratios in-between 0.8-1.0 with no widening of the PDL space which gives conclusions of normal cases. Five (5) images were found with intensity ratios in-between 0.8-1.0 with widening of PDL space up to 25 which gives conclusions of Apical Periodontitis cases. Twelve (12) images were found with intensity ratios in-between 0.25-0.70 with broken PDL space which gives conclusions of Periapical Abscess/Granuloma cases. Five (5) images were found with intensity ratios less than 0.25 with broken PDL space which gives conclusions of Periapical Cyst cases. These radiographs were validated against the gold standard diagnosis. The system achieved high accuracy, precision and recall.

The above described systems and methods can be used for a number of purposes relating to clinical decision making. For example, the systems and methods can: give an early diagnosis of a lesion which prevents the same from spreading and transferring to the next stage; while taking the radiographs, if the exposure level or angulation of cone beam is not proper, the x-ray has to be taken again which increases the radiographic exposure to the patients. Using this tool function, the x-ray can be adjusted and prevented from being taken again therefore it reduces the radiographic exposure level; decrease the probability of re-infection as the lesion has been treated in an early stage; be used to identify a disease so that primary treatments can be performed; help prevent the need for a surgical process like apicoectomy as an infection has been diagnosed and treated in an early stage; save time and increase a patient's comfort; be used to easily find an accessory canal; be used to measure bone loss and determine a stage of bone loss automatically; be used to measure a distance from glenoid fossa to a condylar process which helps in a diagnosis of temporomandibular joint disorders; be used to measure tooth movements during orthodontic treatments; be used to measure how teeth are responding to force of an appliance; be used to measure dental caries and measure an involvement of caries to enamel dentin or pulp; and/or be used to measure a trabecular pattern of an alveolar bone, detecting cracked tooth syndrome. An automatic detection feature can help refresh dentists for the differential diagnosis. It can be useful for the tele-dentistry. It is useful for the rural clinics where dentists visit only one or twice a month. Dental auxiliaries can use this toolbox and make the diagnosis and differential diagnosis ready. This can be an educational tool for the dental students.

Referring now to FIG. 1, there is provided a block diagram of an exemplary computing device 100 that is useful for understanding the present solution. The computing device 100 can include, but is not limited to, a notebook, a desktop computer, a laptop computer, a personal digital assistant, and a tablet PC. Notably, some or all of the components of the computing device 100 can be implemented as hardware, software and/or a combination of hardware and software. The hardware includes, but is not limited to, one or more electronic circuits. The electronic circuits can include, but are not limited to, passive electronic components (e.g., resistors, capacitors, inductors, and/or diodes), active electronic components (e.g., diodes, transistors, integrated circuits, and/or optoelectronic devices), and/or electromechanical components (e.g., terminals, connectors, cable assemblies, switches, and/or protection device).

Notably, the computing device 100 may include more or less components than those shown in FIG. 1. However, the components shown are sufficient to disclose an illustrative embodiment implementing the present solution. The hardware architecture of FIG. 1 represents one architecture of a representative computing device configured to facilitate radiographic images analysis in an efficient manner. As such, the computing device 100 of FIG. 1 implements improved methods for the computerized detection of periapical pathologies.

Notably, the present solution is not limited to a single computer implementation. In some scenarios, the present solution is implemented in a network based system. An exemplary network based system 1400 is provided in FIG. 14. In this case, computing device 100 is communicatively coupled to a server 1404 via a network 1402 (e.g., the Internet or Intranet). The computing device 100 can read data from or write data to a database 1406. Each of the listed components 1402-1406 is well known in the art, and therefore will not be described in detail herein. Any known or to be known network, server and/or data store can be used herein without limitation. Also, cryptography can be used to ensure that cypher text is communicated between devices 100, 1404. The cypher text can include information related to a person's medical history.

As shown in FIG. 1, the computing device 100 includes a system interface 122, a user interface 102, a Central Processing Unit ("CPU") 106, a system bus 110, a memory 112 connected to and accessible by other portions of computing device 100 through system bus 110, and hardware entities 114 connected to system bus 110. At least some of the hardware entities 114 perform actions involving access to and use of memory 112, which can be a Random Access Memory ("RAM"), a disk driver and/or a Compact Disc Read Only Memory ("CD-ROM").

System interface 122 allows the computing device 100 to communicate directly or indirectly with external communication devices (e.g., a remote server or network node). If the computing device 100 is communicating indirectly with the external communication device, then the computing device 100 is sending and receiving communications through a common network (e.g., the Internet or an Intranet).

Hardware entities 114 can include a disk drive unit 116 comprising a computer-readable storage medium 118 on which is stored one or more sets of instructions 120 (e.g., software code) configured to implement one or more of the methodologies, procedures, or functions described herein. The instructions 120 can also reside, completely or at least partially, within the memory 112 and/or within the CPU 106 during execution thereof by the computing device 100. The memory 112 and the CPU 106 also can constitute machine-readable media. The term "machine-readable media", as used here, refers to a single medium or multiple media (e.g., a centralized or distributed database, and/or associated caches and servers) that store the one or more sets of instructions 120. The term "machine-readable media", as used here, also refers to any medium that is capable of storing, encoding or carrying a set of instructions 120 for execution by the computing device 100 and that cause the computing device 100 to perform any one or more of the methodologies of the present disclosure.

In some scenarios, the hardware entities 114 include an electronic circuit (e.g., a processor) programmed for facilitating efficient image processing for medical diagnosis purposes. In this regard, it should be understood that the electronic circuit can access and run Image Analysis and Editing ("IAE") software applications (not shown in FIG. 1) and other types of applications installed on the computing device 100. The IAE software applications are generally operative to facilitate the display of images in an application window, the analysis of images, and the editing of displayed images. An image may be edited to annotate the same. The listed functions and other functions implemented by the IAE software applications are well known in the art, and therefore will not be described in detail herein. As noted above, the IAE software may include Matlab® in some scenarios.

Figure 2:
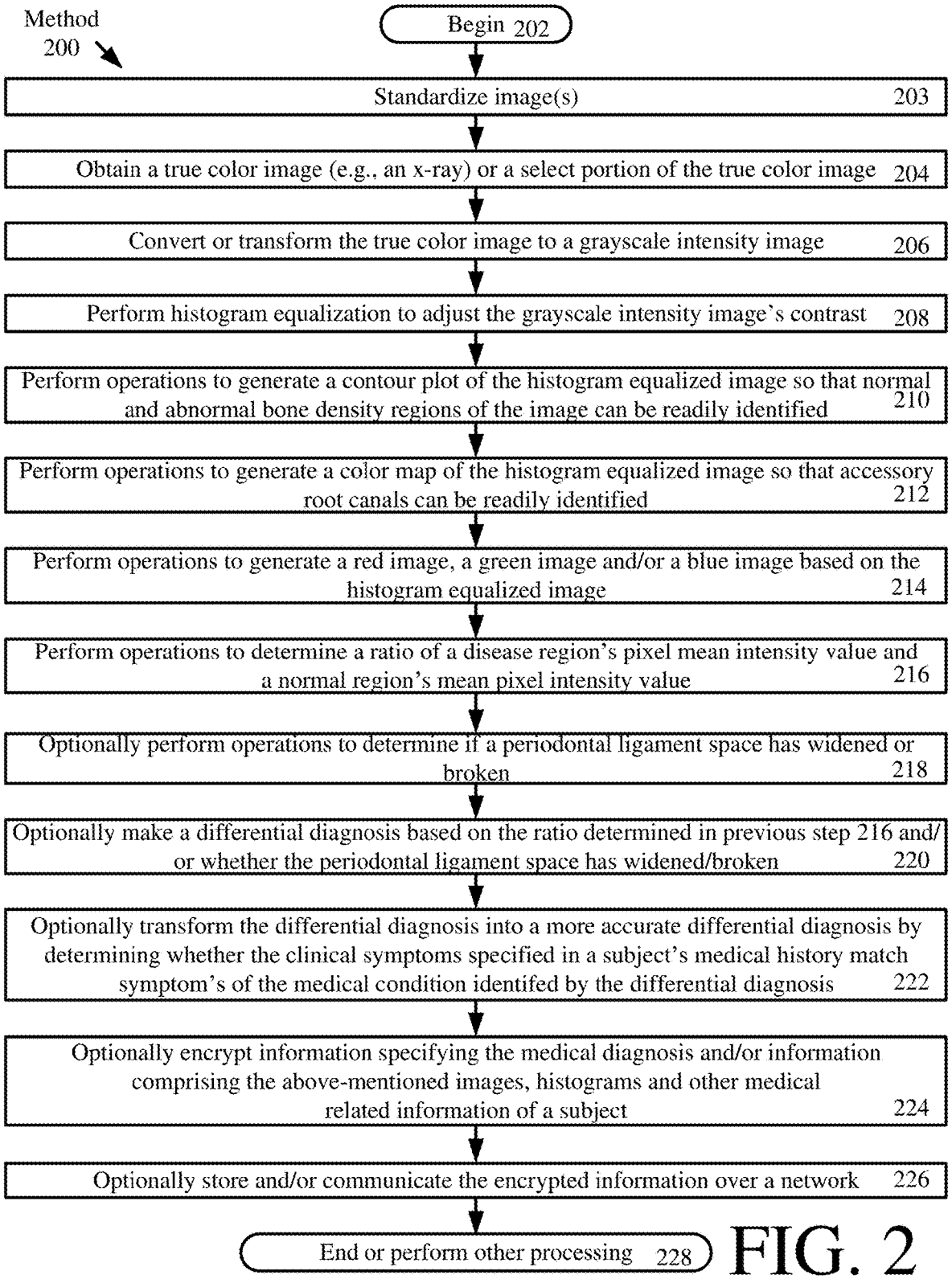
FIG. 2 is a flow diagram of an exemplary method for analyzing an image.

Referring now to FIG. 2, there is provided a flow diagram of an exemplary method 200 for processing an image. In some scenarios, method 200 is performed subsequent to a practitioner's performance of a clinical evaluation and/or the practitioner's performance of operations to obtain x-rays of a portion of the patient's body. However, comprehensive examination x-rays are mandatory. Accordingly, method 200 may also be employed as part of a comprehensive examination.

The method 200 begins with step 202 and continues with step 203. Notably in step 203, all of the images are standardized before any analysis thereof. The standardization is performed because all of the images have different size and mean pixel intensities. In order to make all of them equal, the images have to be standardized to one single size and intensity. Standardization techniques are well known in the art, and therefore will not be described herein. Any known or to be known standardization technique can be used herein without limitation. Notably, the present solution is not limited to the particular order of the steps shown in FIG. 2. For example, the standardization could additionally or alternatively be performed after step 206 or 208.

Figure 3:
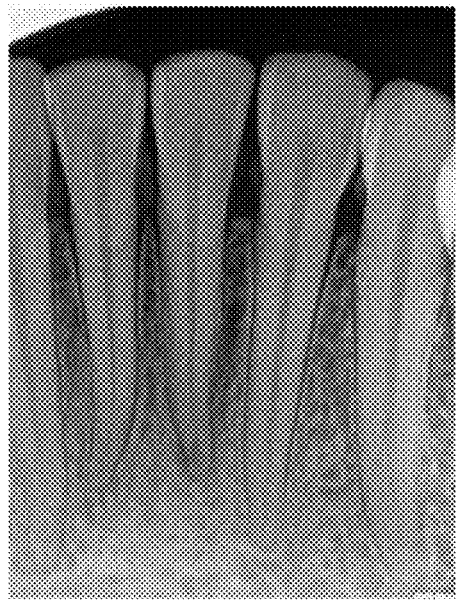
FIG. 3 shows an exemplary true color image.
Figure 14:
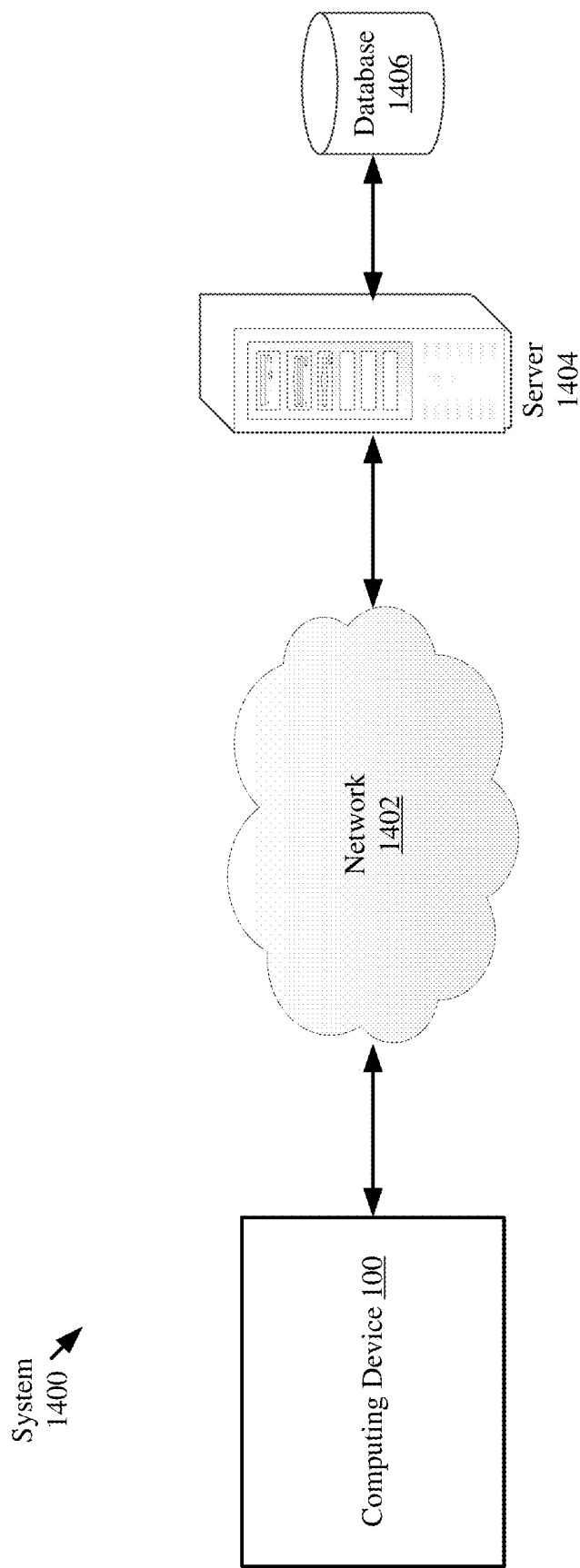
FIG. 14 is an illustration of an exemplary network based system.

In a next step 204, a true color image (e.g., an x-ray) or a portion of the true color image is obtained by a computing device (e.g., computing device 100 of FIGS. 1 and 14). An exemplary true color image is shown in FIG. 3.

In a medical application, the practitioner does not have any diagnosis at this time. As such, the following steps are performed to identify (1) normal and/or disease regions within an image, (2) normal and/or abnormal bone density regions within the image, and/or (3) root canals of an abnormal root formation or in abnormal positions. Information (1)-(3) can be used to confirm or validate a diagnosis made by a medical practitioner.

Figure 4:
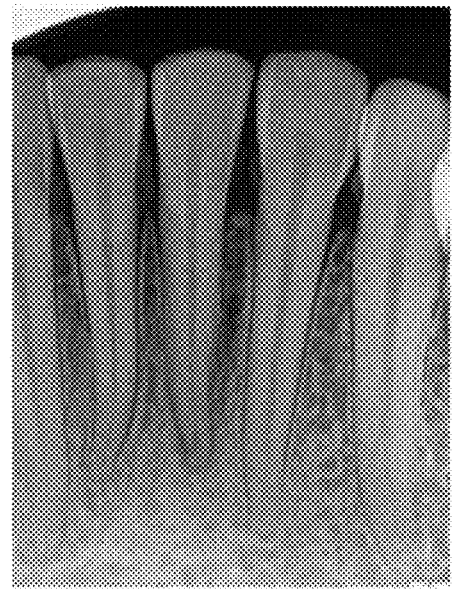
FIG. 4 shows an exemplary grayscale intensity image.

The true color image is then converted or transformed in step 206 by the computing device (e.g., computing device 100 of FIGS. 1 and 14) to a gray scale intensity image. An exemplary grayscale image is shown in FIG. 4. Techniques for converting or transforming a true color image to a gray scale intensity image are well known in the art. Any known or to be known conversion technique can be used herein. In some scenarios, the conversion involves eliminating the hue and saturation information while retaining the luminance.

Figure 5:
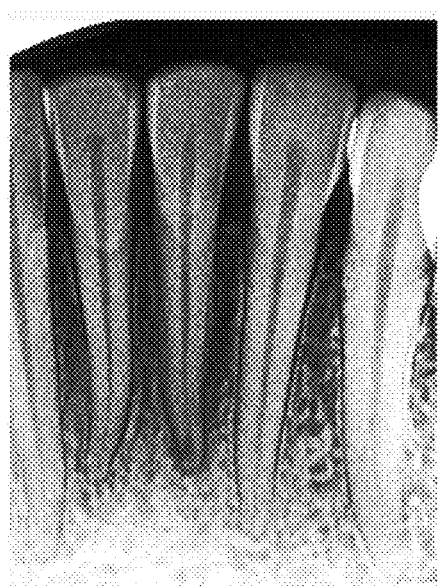
FIG. 5 shows an exemplary histogram equalized image.

Histogram equalization is performed by the computing device (e.g., computing device 100 of FIGS. 1 and 14) to adjust the grayscale intensity image's contrast so that a blurred image is converted to or transformed into a non-blurred image, as shown by step 208. Histogram equalization is well known in the art, and therefore will not be described herein. Any known or to be known histogram equalization techniques can be employed herein without limitation. In some scenarios, the histogram equalization involves increasing the global contrast of the grayscale intensity image so that the intensities are better distributed on the histogram. The intensity distribution is achieved by spreading out the most frequent intensity values. The histogram equalization leads to better views of bone structure and/or tooth structure in an x-ray image, as shown by exemplary x-rays of FIGS. 4 and 5.

Figure 6:
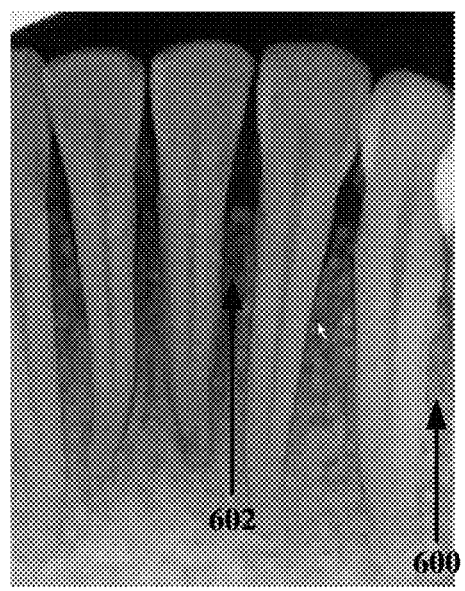
FIG. 6 shows an exemplary contour plot of a histogram equalized image.

In a next step 210, operations are performed by the computing device (e.g., computing device 100 of FIGS. 1 and 14) to generate a contour plot of the histogram equalized image. An exemplary contour plot is shown in FIG. 6. As shown in FIG. 6, the contour plot comprises the histogram equalization image marked with contour lines representing boundaries of a shape (e.g., boundaries of each tooth). Techniques for generating contour plots are well known in the art. Any known or to be known contour plot technique can be used herein without limitation. The contour plot allows a viewer to more easily identify regions of the image with normal bone density and regions of the image with bone loss. For example, in FIG. 6, light gray region 600 illustrates normal bone density and dark gray/black region 602 represents abnormal bone density (or bone loss between two adjacent teeth). Such abnormal bone density or bone loss indicates that the patient suffers from Periodontitis (i.e., an inflammatory disease affecting the tissue that surrounds and supports the teeth and bone loss). Periodontitis involves the progressive loss of the alveolar bone around the teeth, and if left untreated could lead to tooth loss.

Figure 7:
FIG. 7 shows an exemplary color map of a histogram equalized image.

Upon completing step 210, operations are performed in step 212 by the computing device (e.g., computing device 100 of FIGS. 1 and 14) to generate a color map of the histogram equalized image. An exemplary color map is shown in FIG. 7. These operations involve color coding the image for purposes of clearly differentiating structures thereof. In some scenarios, the color map allows canals to be more easily identified so as to decrease complications associated with routine root canal procedures. Such complications can arise when a root canal has been missed. In this regard, it should be understood that sometimes a dentist can miss an accessory canal if the tooth has more canals than anticipated or if it is in an abnormal position. If this happens bacteria can remain in the infected canal and re-contaminate the tooth.

Figure 8:
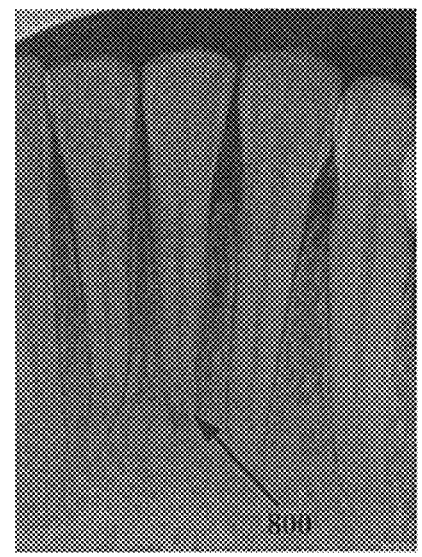
FIG. 8 shows an exemplary green image.

Next step 214 involves performing operations to generate a red image, a green image and/or a blue image based on the histogram equalized image. An exemplary green image is shown in FIG. 8. In some scenarios, the operations involve: extracting green and blue color from an image so as to leave only the red color therein; extracting the red and blue color from the image so as to leave only the green color therein; and/or extracting the green and red color from the image so as to leave only the blue color therein. In some scenarios, the red, green and/or blue images allow variations in canal dimensions (e.g., diameters) to be more easily identified. For example, a periapical abscess 800 occurring at the tip of root canal is more easily seen in a green image of FIG. 8 as compared to a true color image of FIG. 3 and/or a grayscale intensity image of FIG. 4.

Next step 216 involves performing operations by the computing device (e.g., computing device 100 of FIGS. 1 and 14) to determine a ratio of a disease region's mean pixel intensity value and a normal region's mean pixel intensity value. In some scenarios, an x-ray image obtained for the patient and/or other subjects are used here. This step can be performed automatically or in response to a user input selecting two regions of interest within a displayed image. Pixel intensity values are well known in the art, and therefore will not be described in detail herein. However, it should be understood that a pixel intensity value describes how bright a respective pixel is and/or what color the respective pixel should be. For grayscale images, the pixel intensity value is a single number that represents the brightness of the pixel. A pixel intensity value typically comprises an 8-bit integer with a value between 0 and 255. A pixel intensity value of 0 typically indicates that the pixel's color is black. A pixel intensity value of 255 indicates that the pixel's color is white. Values in between 0 and 255 represent shades of gray. For a color image, the pixel intensity value is represented as a vector of three numbers for the R, G and B components.

Figure 15:
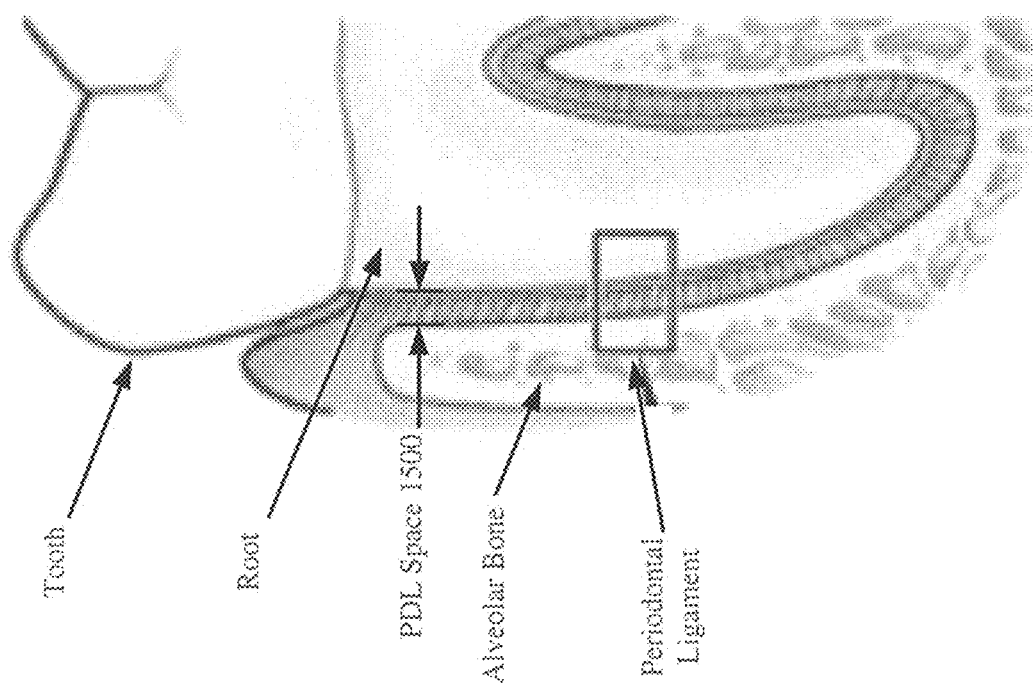
FIG. 15 is an illustration of a PDL space.

A PDL space (e.g., PDL space 1500 of FIG. 15) may also be determined in optional step 218 by the computing device (e.g., computing device 100 of FIGS. 1 and 14). As should be understood, a PDL is a space that surrounds and attaches roots of teeth to the alveolar bone, as shown in FIG. 15.

In some scenarios, the ratio determined in step 216 and/or the PDL space determined in step 218 can be used to make a differential diagnosis, as shown by optional step 220. For example, a diagnosis of no abnormality/pathogenesis is made when the ratio has a value between 0.8 and 1.0 and no widening of a PDL space exists. A diagnosis of an apical periodontitis is made when the ratio has a value between 0.8-1.0 and a widening of the PDL space up to 25. A diagnosis of a periapical abscess/granuloma is made when the ratio has a value in-between 0.25-0.70 and a broken PDL space exists. A diagnosis of a periapical cyst or periapical abscess is made when the ratio has a value less than 0.25 and a broken PDL space exists.

In some scenarios, the differential diagnosis is converted or transformed into a more accurate differential diagnosis as shown by optional step 222. This conversion or transformation is achieved using the subject's medical records or history. More specifically, a determination is made as to whether clinical symptoms specified in the subject's medical records or history match clinical symptoms of a medical condition identified by the differential diagnosis. If so, the accuracy of the medical condition is verified or validated. In not, the medical diagnosis is determined to be inaccurate. Accordingly, the first information and medical record information is re-analyzed to derive the more accurate medical diagnosis.

In a next optional step 224, the computing device (e.g., computing device 100 of FIGS. 1 and 14) optionally encrypts information specifying the medical diagnosis and/or information comprising the above-mentioned images, histograms and other medical information of a subject. Encryption can be employed for purposes of complying with at least the Health Insurance Portability and Accountability Act ("HIPAA") confidentiality requirements. The encryption is achieved using a chaotic, random or pseudo-random number based algorithm. Any known or to be known chaotic, random or pseudo-random number based algorithm can be used herein without limitation. A seed value for the chaotic, random or pseudo-random number based algorithm can be selected from a plurality of pre-defined seed values or dynamically generated during operations of the first computing device. The term "seed value", as used herein, refers to a starting value for generating a sequence of chaotic, random, or pseudo-random integer values. The seed value(s) can be selected or generated based on information relating to the human or animal subject (e.g., an identifier, an address, a phone number, an age, a medical diagnosis, a medical symptom, information contained in a medical history, a ratio of a disease region's mean intensity value, a normal region's mean pixel intensity value, a periodical ligament space, and/or any other value).

Subsequently, optional step 226 is performed where the encrypted information is stored (e.g., in memory 112 of FIG. 1) and/or communicated over a network (e.g., network 1402 of FIG. 14) from the first computing device to a remote second computing device (e.g., server 1404 of FIG. 14) for storage in a data store (e.g., database 1406 of FIG. 14) and/or subsequent processing. At the second computing device, the encrypted information may be decrypted. Methods for decrypting data are well known in the art, and therefore will not be described herein. Any known or to be known decryption technique can be used herein without limitation. Upon completing step 226, step 228 is performed where method 200 ends or other processing is performed.

In some scenarios, method steps 210-226 can optionally be performed automatically by a computing device with no or minimal user input. In this case, medical diagnosis can be made by the computing device, and abnormal areas of an image can be identified automatically during image processing operations performed by the computing device. Exemplary images generated by the computing device performing such automatic operations are shown in FIGS. 9-13.

Figure 9:
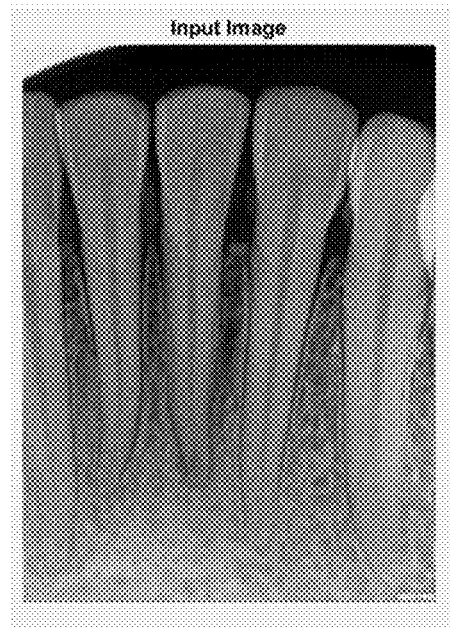
FIG. 9 shows a normal original image input to an automatic image analysis process.

FIG. 9 shows a normal original image input to an automatic image analysis process. In a Matlab® context, IM2=imophat(IM,SE) performs morphological top-hat filtering on the grayscale or binary input image IM. Top-hat filtering computes the morphological opening of the image (using impen) and then subtracts the result from the original image. Imophat uses the structuring elements SE, where SE is returned by strel. SE must be a single structuring element object, not an array containing multiple structuring element objects.

Figure 10:
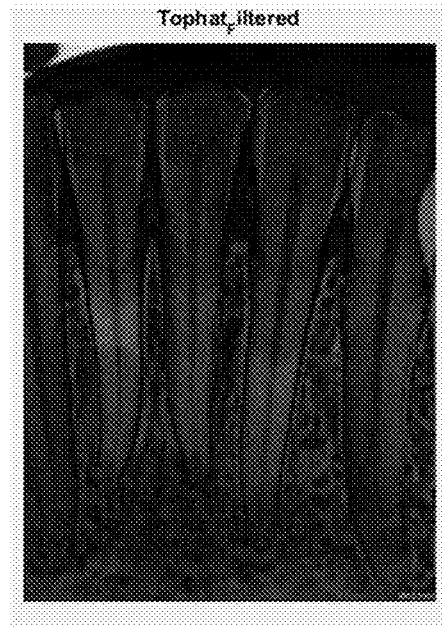
FIG. 10 shows an image resulting from an automatic image analysis process.
Figure 11:
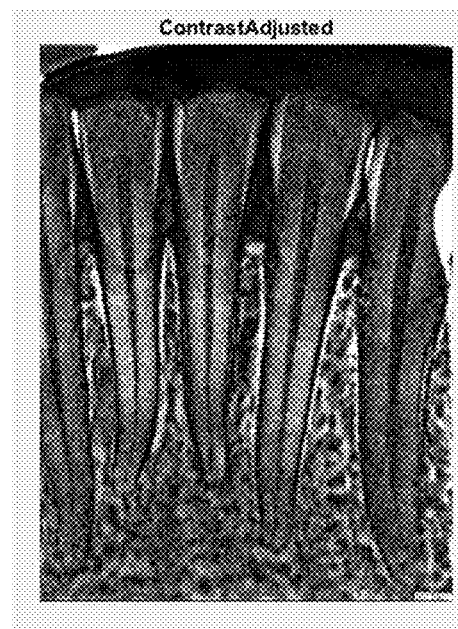
FIG. 11 shows a contrast adjusted image resulting from an automatic image analysis process.
Figure 12:
FIG. 12 shows a histogram equalized image resulting from an automatic image analysis process.
Figure 13:
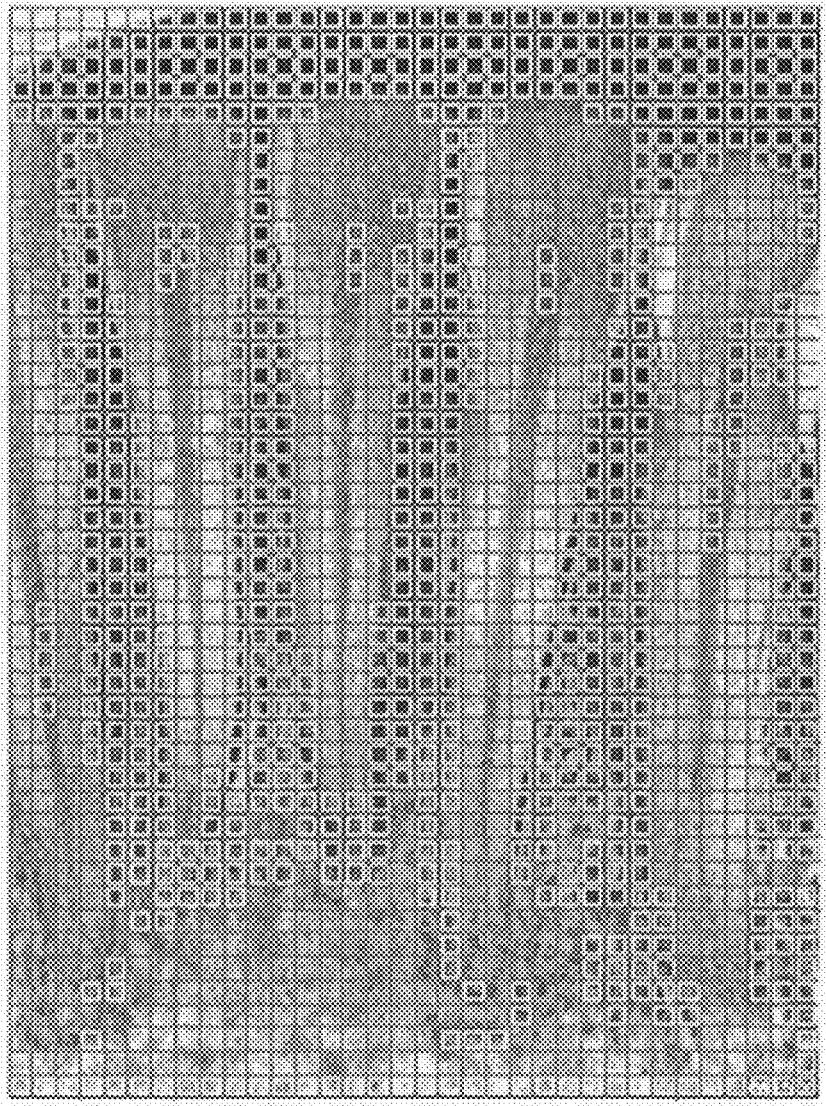
FIG. 13 shows an image with boxes overlaid thereon showing radiolucent regions thereof.

FIG. 10 shows an image resulting from an automatic image analysis process. FIG. 11 shows a contrast adjusted image resulting from an automatic image analysis process. Contrast adjustment is performed for providing a better understanding of alveolar bony pattern. FIG. 12 shows a histogram equalized image resulting from an automatic image analysis process. In a Matlab® context, histeg works on the entire image and adapthisteg operates on small regions of the image, called tiles. Each tile's contrast is enhanced, so that the histogram of the output region approximately matches a specified histogram. After performing the equalization, adapthisteg combines neighboring tiles using bilinear interpolation to eliminate artificially induced boundaries. FIG. 13 shows an image with boxes overlaid thereon showing radiolucent regions thereof.

Notably, the present technique may employ machine learning for disease diagnosis purposes. The machine learning may be based on pre-stored patterns, manual inputs, and/or results of previous image analysis. Machine learning techniques are well known in the art. Any known or to be known machine learning technique can be used herein without limitation.

The present solution is not limited to the particular order in which steps of method 200 are performed. In this regard, it should be noted that in method 200 image processing is performed to make a first differential diagnosis and clinical symptoms are used to generate a more accurate second differential diagnosis and/or validate the accuracy of the first differential diagnosis. In other scenarios, the order of this process is reversed, i.e., the clinical symptoms are used to generate a first differential diagnosis and the results of the image processing are used to generate a more accurate second differential diagnosis and/or validate the accuracy of the first differential diagnosis. A flow diagram illustrating this reverse process is provided in FIG. 16.

Figure 16:
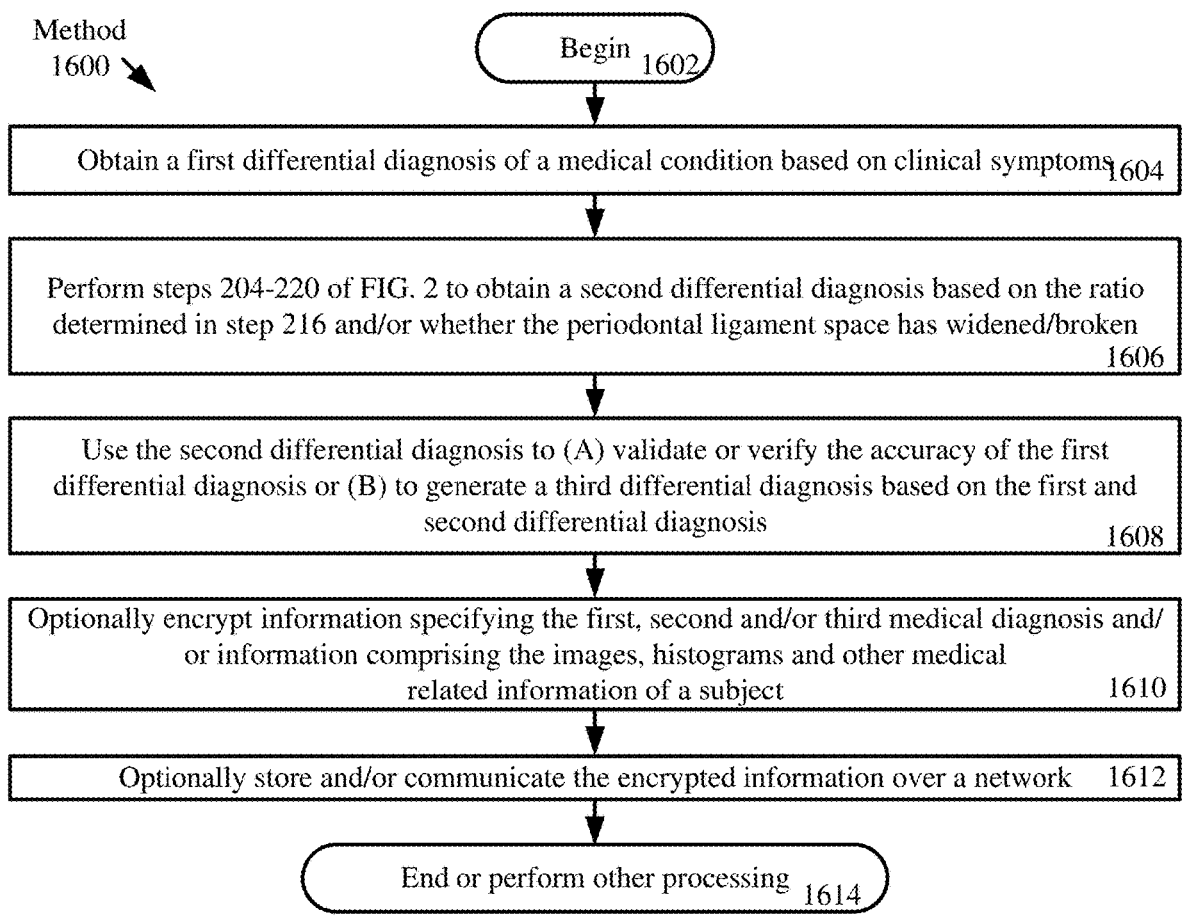
FIG. 16 is a flow diagram of an exemplary for generating an accurate medical diagnosis.

Referring now to FIG. 16, method 1600 begins with step 1602 and continues with step 1604 where a first differential diagnosis of a medical condition is obtained based on clinical symptoms. The medical condition can include, but is not limited to, an abscess, a chronic apical abscess, a periapical granuloma or an apical periodontal cyst. Each of the medical conditions is defined below along with its clinical symptoms.

An abscess consists of a collection of pus into a cavity formed by tissue liquefaction caused by bacterial infection. It can be of acute onset or chronic in nature. A patient with acute lesions experiences mild to severe pain which may be rapid, spontaneous and extreme in nature and swelling of associated tissues. The pain can be relieved by applying pressure on tooth. In most cases, the tooth is extremely sensitive to percussion. Vitality test is negative and tooth may be extruded in the socket. Trismus may occur. Systemic manifestations may also develop, including fever, lymphadenopathy, malaise, headache, and nausea. Radiographically lesion may not show the bone destruction as it develops very quickly. In most cases, the tooth is extremely sensitive to percussion. Vitality test is negative.

Chronic apical abscess lesions are gradual onset, little or no discomfort and an intermittent discharge of pus through an associated draining sinus tract which opens in gingivobuccal/gingivolabial sulcus. Sinus tract is present in most of cases which can be confirmed by gutta percha test and taking radiographs. Radiographically, there are typically signs of osseous destruction such as a radiolucency.

Periapical granuloma is generally symptomless, usually diagnosed on radiographs as well circumscribed lesions. Slight tender to percussion may be present and produce dull sound due to presence of granulation tissue at the apex of involved non-vital tooth. Mild pain on chewing or biting may be reported. No cortical plate perforations or sinus tracts are seen unless acute exacerbations into abscesses.

Apical periodontal cyst, Periapical cyst or Radicular cyst is asymptomatic lesions with no clinical presentations. They are painless and tender to percussion is absent if not secondarily infected. They expand over period of time and rarely cause expansion of cortical plates to be visible clinically as swelling.

Referring again to FIG. 16, method 1600 continues with step 1606. Step 1606 involves performing steps 204-220 of FIG. 2 to obtain a second differential diagnosis based on the ratio determined in step 216 and/or whether the periodontal ligament space has widened and/or broken. The second differential diagnosis is then used in step 1608 to: (A) validate or verify the accuracy of the first differential diagnosis; and/or (B) to generate a third differential diagnosis based on the first and second differential diagnosis. There-after, optional steps 1610-1612 can be performed. These steps involve: optionally encrypting information specifying the first, second and/or third medical diagnosis and/or information comprising the images, histograms and other medical related information of a subject; storing the encrypted information in a data store; and/or communicating the encrypted information over a network. Subsequently, step 1614 is performed where method 1600 ends or other processing is performed.

In some scenarios, the present solution can be extended to artificial neural network and rule based knowledge systems within the Peri-lesions differential diagnosis tool. This program performs classification, taking as input a set of findings that describe a given case and generates as an output a set of numbers, where each output corresponds to the likelihood of a particular classification that could explain the findings. The rule based decision support system is a type of knowledge based clinical decision support system. The rules and associations of compiled data which most often take the form of IF-THEN rules. For instance, if this is a system for determining periapical lesions, then a rule might be that IF radiolucency is <1 mm AND IF pain present on percussion AND IF periodontal ligament space broken THEN periapical abscess.

Within the section "periapical lesions clinical findings explanation", clinical findings of each periapical lesions (abscess, granuloma and cyst) are described by certain text found in the definitions provided above. This text describes the clinical findings and symptoms from the patients. These are additional to the radiographs. Usually, these findings are documented before the radiograph are taken. While involving these findings, developing rules and radiographic findings can accelerate the diagnosis accuracy.

The above mentioned text (or keywords) for the clinical findings are recorded either in the structured format or un-structured format. Structured data refers to information with a high degree of organization. The data is easy to analyze. Unstructured data refer to information with disorganization of information such as free text. Unstructured data is difficult to analyze. Different academia uses different formats to record the information. If they are recorded with the structured format, then it is easy to retrieve the information. If these findings are documented in unstructured format (free-text) then information can be extracted automatically using natural language processing techniques. Once the information is extracted, it can be combined with the radiographic findings and final diagnosis can be achieved. After the clinical finding and radiographic findings are gathered, the diagnosis will be made automatically by the system.

All of the apparatus, methods, and algorithms disclosed and claimed herein can be made and executed without undue experimentation in light of the present disclosure. While the invention has been described in terms of preferred embodiments, it will be apparent to those having ordinary skill in the art that variations may be applied to the apparatus, methods and sequence of steps of the method without departing from the concept, spirit and scope of the invention. More specifically, it will be apparent that certain components may be added to, combined with, or substituted for the components described herein while the same or similar results would be achieved. All such similar substitutes and modifications apparent to those having ordinary skill in the art are deemed to be within the spirit, scope and concept of the invention as defined.

The features and functions disclosed above, as well as alternatives, may be combined into many other different systems or applications. Various presently unforeseen or unanticipated alternatives, modifications, variations or improvements may be made by those skilled in the art, each of which is also intended to be encompassed by the disclosed embodiments.

I claim:

1. A method for generating a medical and/or dental diagnosis, comprising:
   obtaining, by a computing device, a true color image of a select part of a subject's body;
   converting, by the computing device, the true color image to a grayscale intensity image;
   generating, by the computing device, a histogram equalized image by adjusting the grayscale intensity image's contrast;
   processing, by the computing device, the histogram equalized image to generate first information useful for generating the medical and/or dental diagnosis, the first information comprising
   (a) a ratio of a disease region's pixel mean intensity value and a normal region's mean pixel intensity value and (b) an indicator indicating whether a periodontal ligament space has widened or broken, or
   only (b) an indicator indicating whether a periodontal ligament space has widened or broken; and
   generating, by the computing device, the medical and/or dental diagnosis based at least on the first information.

2. The method according to claim 1, wherein the processing involves generating a contour plot of the histogram equalized image so that normal and abnormal bone density regions of the histogram equalized image are identifiable.

3. The method according to claim 1, wherein the processing involves generating a color map of the histogram equalized image so that root canals are identifiable.

4. The method according to claim 1, wherein the processing involves generating a red image, a green image, or a blue image so that variations in canal dimensions are identifiable.

5. The method according to claim 1, further comprising transforming the medical and/or dental diagnosis into a more accurate medical and/or dental diagnosis using clinical symptoms specified in the subject's medical records.

6. The method according to claim 5, wherein the transforming involves determining whether the clinical symptoms match specified in the subject's medical records match clinical symptoms of a medical condition identified by the medical and/or dental diagnosis.

7. The method according to claim 1, wherein the medical and/or dental diagnosis is generated based additionally on clinical symptoms specified in the subject's medical records.

8. The method according to claim 7, wherein medical and/or dental diagnosis is generated by:
   obtaining a first differential diagnosis based on the clinical symptoms; and
   validating an accuracy of the first differential diagnosis using the first information.

9. The method according to claim 7, wherein medical diagnosis is generated by:
   obtaining a first differential diagnosis based on the clinical symptoms;
   obtaining a second differential diagnosis based on the first information; and
   determining the medical and/or dental diagnosis based on the first differential diagnosis and second differential diagnosis.

10. The method according to claim 1, further comprising encrypting information specifying the medical and/or dental diagnosis prior to being stored in a data store or communicated over a network.

11. A system for generating a medical and/or dental diagnosis, comprising:
   at least one processor;
   a non-transitory computer-readable medium comprising programming instructions that, when executed, cause the at least one processor to perform data processing operations at a computing device, wherein the programming instructions comprise instructions to:
      obtain a true color image of a select part of a subject's body;
      convert the true color image to a grayscale intensity image;
      generate a histogram equalized image by adjusting the grayscale intensity image's contrast;
      processing the histogram equalized image to generate first information useful for generating the medical and/or dental diagnosis, the first information comprising
         (a) a ratio of a disease region's pixel mean intensity value and a normal region's mean pixel intensity value and (b) an indicator indicating whether a periodontal ligament space has widened or broken, or
         only (b) an indicator indicating whether a periodontal ligament space has widened or broken; and
      generate the medical and/or dental diagnosis based at least on the first information.

12. The system according to claim 11, wherein the histogram equalized image processing involves generating a contour plot of the histogram equalized image so that normal and abnormal bone density regions of the histogram equalized image are identifiable.

13. The system according to claim 11, wherein the histogram equalized image processing involves generating a color map of the histogram equalized image so that root canals are identifiable.

14. The system according to claim 11, wherein the histogram equalized image processing involves generating a red image, a green image, or a blue image so that variations in canal dimensions are identifiable.

15. The system according to claim 11, wherein the programming instructions further comprise instructions to transform the medical and/or dental diagnosis into a more accurate medical and/or dental diagnosis using clinical symptoms specified in the subject's medical records.

16. The system according to claim 15, wherein the medical and/or dental diagnosis is transformed based on results of a determination as to whether the clinical symptoms match specified in the subject's medical records match clinical symptoms of a medical condition identified by the medical and/or dental diagnosis.

17. The system according to claim 11, wherein the medical and/or dental diagnosis is generated based additionally on clinical symptoms specified in the subject's medical records.

18. The system according to claim 17, wherein medical and/or dental diagnosis is generated by:
   obtaining a first differential diagnosis based on the clinical symptoms; and
   validating an accuracy of the first differential diagnosis using the first information.

19. The system according to claim 17, wherein medical and/or dental diagnosis is generated by:
   obtaining a first differential diagnosis based on the clinical symptoms;
   obtaining a second differential diagnosis based on the first information; and
   determining the medical and/or dental diagnosis based on the first differential diagnosis and second differential diagnosis.

20. The system according to claim 11, wherein the programming instructions further comprise instructions to encrypt information specifying the medical and/or dental diagnosis prior to being stored in a data store or communicated over a network.

* * * * *